United States Patent [19]

Kuhlemann et al.

[11] Patent Number: 4,530,697
[45] Date of Patent: * Jul. 23, 1985

[54] NEEDLE ASSEMBLY

[75] Inventors: Bruce N. Kuhlemann, Hayward; Kalman Horvath, Concord; Prentice C. Wharff, Oakley, all of Calif.

[73] Assignee: Miles Laboratories, Inc., Elkhart, Ind.

[ * ] Notice: The portion of the term of this patent subsequent to Mar. 6, 2001 has been disclaimed.

[21] Appl. No.: 461,325

[22] Filed: Jan. 27, 1983

Related U.S. Application Data

[63] Continuation-in-part of Ser. No. 386,549, Jun. 9, 1982, Pat. No. 4,435,177.

[51] Int. Cl.³ .............................................. A61M 5/32
[52] U.S. Cl. ..................................... 604/263; 604/199
[58] Field of Search ............................... 604/192–199, 604/263

[56] References Cited

U.S. PATENT DOCUMENTS

| 2,578,813 | 12/1951 | Kollsman | 604/263 X |
| 3,523,530 | 8/1970 | Pagones et al. | 604/263 |
| 4,085,737 | 4/1978 | Bordow | 604/263 X |
| 4,091,811 | 5/1978 | Bates et al. | 604/263 |
| 4,435,177 | 3/1984 | Kuhlemann et al. | 604/263 |

Primary Examiner—Dalton L. Truluck
Attorney, Agent, or Firm—Theodore J. Leitereg; James A. Giblin

[57] ABSTRACT

There is disclosed a needle assembly comprising a needle, a needle-retaining portion, a removable needle protector portion, and a resilient member for removing liquid from the surface of the needle which is disposed around the needle rearward of its point. The liquid removing member has a needle-accommodating opening with a diameter approximately that of the outside diameter of the needle. The member is contained within the needle protector portion and removable from the needle with the removal of the needle protector portion from the assembly. Also disclosed are blood bag systems comprising a donor bag and the aforementioned needle assembly.

16 Claims, 8 Drawing Figures

NEEDLE ASSEMBLY

CROSSREFERENCE TO RELATED APPLICATION

This is a continuation-in-part of co-pending application U.S. Ser. No. 386,549, filed June 9, 1982, now U.S. Pat. No. 4,435,177 issued Mar. 6, 1984.

BACKGROUND OF THE INVENTION

1. Field of the Invention

This invention relates to and has among its objects the provision of novel needle assemblies. It is a particular object of the present invention to provide a needle assembly for use in the collection of blood from a donor. Further objects of the invention will be evident from the following description wherein parts and percentages are by weight unless otherwise specified.

2. Description of the Prior Art

In conventional blood banking practice, blood is collectedd from a donor into a sterile, flexible, plastic container (donor bag), which is usually part of a blood bag system to be used in the processing of the collected blood into components. The donor bag generally contains an anticoagulant which mixes with the collected blood. Attached to the donor bag by means of flexible tubing is a needle for making a venipuncture in the donor's arm. It is, or course, mandatory to maintain the sterile integrity of the needle used for the venipuncture. If the needle is contaminated it could be dangerous to the blood donor, and the contamination could be washed into the collected blood. The needle should operate with minimal discomfort to the donor.

Conventional donor needles usually comprise a needle normally with a sharpened forward end for the venipuncture, a needle-retaining means, and a needle protector. Customarily, blood bag systems are sterilized after assembly. During the sterilization procedure droplets of anticoagulant may enter the needle and pass into the needle protector. This anticoagulant liquid adheres to the needle surface and during venipuncture may cause an unpleasant stinging sensation in a donor or at least cause apprehension in the mind of a donor. Removal of the liquid by wiping the needle surface after the needle protector is removed is difficult because sterility must be maintained.

Some workers have approached the above problem by designing a needle protector with a front portion with an inside diameter approximately the same diameter as the needle's outside diameter, therefore fitting tightly around the needle (U.S. Pat. No. 3,523,530). In this way anticoagulant solution in a donor bag is kept from leaking out of the needle and filling the protector. However, such an approach is less than satisfactory for removing residual liquid on the full surface of the needle. Such liquid may get in the needle protector during sterilization of the blood bag assembly. Steam sterilization is generally employed and causes the anticoagulant in the donor bag to vaporize, a situation which is actually necessary for the sterilization of the needle.

It is also known to imbed the needle in a rubber or cork stopper (U.S. Pat. Nos. 2,688,963; 2,667,163; 2,688,964; 3,416,657). However, this approach is disadvantageous not only because of the deleterious impact on sterilization but also because the needle point may become either damaged or coated with particles or both.

Other needle assemblies for parenteral use are known in the art. For example, donor needles for blood donor assemblies are described in U.S. Pat. Nos. 2,689,562 and 4,091,811. U.S. Pat. Nos. 2,938,238; 3,406,687; and 3,523,531; disclose needle assemblies for parenteral administration; and syringes are disclosed in U.S. Pat. Nos. 2,708,438; 1,494,973; and 3,416,657.

SUMMARY OF THE INVENTION

The invention described herein is a needle assembly comprising a needle, a needle-retaining portion, a needle protector portion, and a resilient member positioned around a portion of, and disposed rearward of the point of, said needle in a fashion to remove liquid from the surface of the needle. The liquid removing member has a needle-accommodating opening with a diameter approximately that of the outside diameter of the needle. The liquid-removing member is contained within the needle protector portion and is removable from the needle with the removal of the needle protector portion from the needle assembly.

Further, this invention provides a blood bag assembly comprising a flexible blood bag with flexible tubing and outlet ports attached thereto. The needle assembly of the invention is attached to the flexible tubing and allows for venipuncture into the donor's arm. The blood bag assembly may comprise only a donor or collection bag or it may include a donor bag and one or more satellite bags for the collection of blood and the processing of the collected blood into components.

The primary advantage of the invention is that the needle, with the needle protector and liquid-removing member removed, is free of a substantial portion of any liquid which otherwise might be present on the needle surface. With respect to blood collection, discomfort to the donor is minimized. Furthermore, the needle assembly of the invention provides for maximum maintenance of sterility of the needle surface. Thus, the danger of contamination of the donor or the collected blood is minimized.

DESCRIPTION OF THE PREFERRED EMBODIMENTS

The invention will be described in detail with reference to the attached drawings. In the following description emphasis is directed to a blood bag assembly with the instant needle assembly. This emphasis is by way of example only and is not meant to limit the invention.

The present needle assembly may be adapted to all kinds of parenteral use where the presence of liquid on the surface of a needle is to be minimized.

Figure 1:
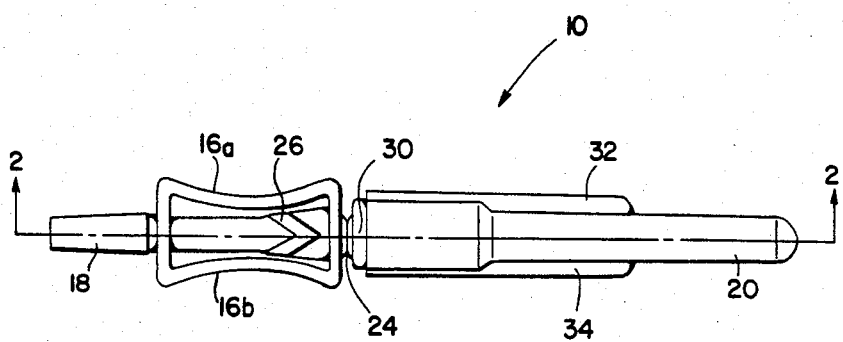
FIG. 1 is a top plan view of a needle assembly in accordance with the invention.
Figure 2:
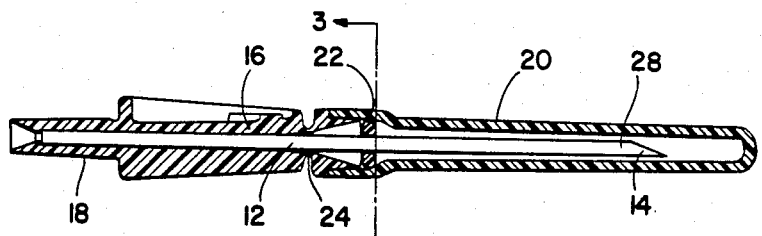
FIG. 2 is a sectional view taken along line 2—2 of FIG. 1.
Figure 3:
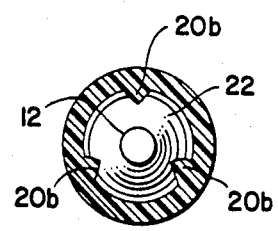
FIG. 3 is based on FIG. 2 but depicts an alternate embodiment of the present invention.

The details of needle assembly 10 are best seen in FIGS. 1-3. As shown in these figures the needle assembly includes a needle 12 sharpened at its forward end 14. AT its rearward end the needle is permanently retained in a bore in needle-retaining means 16, which has indentations 16a and 16b and thus may also serve as a handle or hub section to be grasped in the use of assembly 10. Preferably, means 16 has a slanted bottom surface 16c so that means 16 may fit closely to a donor's arm when the needle assembly is in use. The needle is retained in 16 by means of an adhesive or the like or other suitable modes of retention known in the art. Retaining means 16 may be formed from a rigid or non-rigid material such as a medically acceptable thermoplastic, for example, polystyrene, polycarbonate, rigid polyvinylchloride, and the like. Retaining means 16 has a narrowed, tube-receiving section 18 at its rear designed to fit inside flexible tubing 20 such as that found on a blood bag. Thus, the needle's passage is directly connected through section 18 to the passage of such flexible tubing. The forward part of means 16 is designed to receive needle protector 20, which surrounds needle 12 and protects the needle's sterility. Protector 20 is bonded to retaining means 16 by means of an adhesive or other suitable bonding material. Generally, needle protector 20 is formed of a rigid or non-rigid plastic such as that used for needle-retaining means 16. Once assembled, the combination of needle protector 20 and retaining means 16 acts as a one-piece unit. Other modes of forming a needle and protector combination will be evident to those skilled in the art and are contemplated in the present invention.

Surrounding needle 12 at its rearward end at a point near the handle or hub section is flexible resilient member 22 made of rubber, medical grade elastomer, or the like. Member 22 has a needle-accommodating opening having a diameter approximately that of the outside diameter of needle 12, thus providing a positioning of the needle-contacting portion of member 22 about needle 12 and exerting a certain inward pressure on needle 12 such that liquid on the surface of the needle will be removed as member 22 is disengaged from needle 12. Thus, the diameter of the opening should be such as to provide a gentle, liquid-removing wiping action on the needle surface without causing damage to the needle surface including any lubricant on the needle surface such as a silicone coating. Preferably, the opening of 22 should be slightly smaller, about 4-10%, than the outside diameter of the needle. In another preferred arrangement the diameter of the opening is such that the lubricating coating on the needle surface is distributed evenly by the action of member 22, thus providing a significant reduction, usually about 25% or more, in the shaft drag of the needle upon its insertion into the arm of a donor. Member 22 may take the form of a rubber ring or a rubber septum (22a in FIG. 3).

Figure 5:
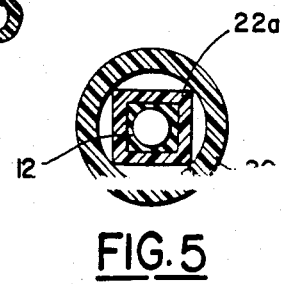
FIG. 5 is a cross sectional view of FIG. 4 as shown at line 5—5.

As can be seen from FIGS. 1 and 2 the rearward portion 20a of protector 20 is flanged outwardly such that the inside diameter of the rear portion of 20 is larger than the inside diameter of the front portion of 20. Member 22 is positioned entirely within the rearward portion of protector 20. Referring now to FIG. 3 the enlarged rear portion 20a of protector 20 has a plurality of inwardly protruding ribs 20b for retainment of 22 within 20a. As can be seen in FIG. 3, the outside diameter of 22 is smaller than the inside diameter of 20 at portion 20a. This allows the portion of the assembly rearward of member 22 to be sterilized during the steam sterilization procedure. As described above, during steam sterilization of the blood bag assembly, vaporized anticoagulant solution enters the needle protector resulting in sterilization. Member 22 must be designed to permit sterilization of the entire area inside the needle protector. Other designs of member 22 to achieve this result will be suggested to those skilled in the art from the teaching contained herein. For example, in FIG. 5 septum 22a is square shaped, thus providing passage of vaporized anticoagulant solution on both sides of 22a within protector 20. The outside diameter of member 22a at its four corners is slightly larger than the inside diameter of the rearward portion of 20 thus allowing a member 22a to be held in protector 20 by means of friction. Member 22 may also have an elliptical shape for the above purpose.

Needle-retaining means 16 has a narrowed portion at a point immediately rearwardd of needle protector 20, with peripheral, frangible, circumferential groove 24 which provides for a thickness preferably of about 0.012±0.001 mm at its narrowest point. In general, groove 24 is designed to facilitate the removal of needle protector 20 and a portion of means 16 from needle assembly 10 by twisting to rupture groove 24. The needle assembly 10 additionally includes a raised portion 26, in retaining means 16, which may take the form of an arrowhead to show the orientation of bevel 28 of the sharpened end of the needle when it is hidden from view, e.g., by being placed in the arm of a donor. The point of 26 may also be aligned during assembly with line marker 30 forward of groove 24. In this respect portion 26 in conjunction with line 30 acts to provide a tamper-evident feature to assembly 10. Thus, it may be readily evident to the user, simply by tactily sensing the integrity of groove 24 and/or looking at the position of 26 and 30, whether the needle assembly has been tampered with and sterility breached.

In the above there has been described a particular tamper-evident feature, which renders the needle assembly tamper-proof. It is of course possible to employ another tamper-evidencing feature in the needle assembly of the invention.

Protector 20 further comprises integral flanges 32 and 34 which provide suitable gripping means for rotating the protector to disengage the front portion of the needle assembly from the rear portion along groove 24.

Figure 4:
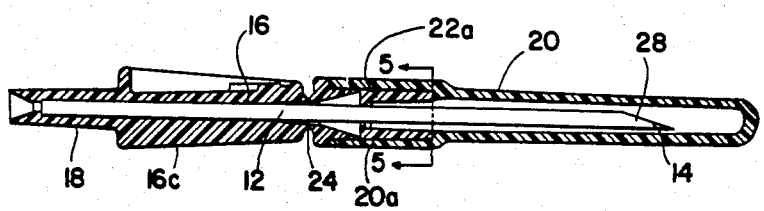
FIG. 4 is a front elevational view of a blood bag containing a needle assembly in accordance with the invention attached to the blood bag by means of flexible tubing.

Referring now to FIG. 4 there is shown flexible blood bag 36 having at its top end fitment 38 with donor (collection) tubing 40 and additional ports 42, 44, and 46, with tear-off caps 48, 50, and 52, respectively. However, any one of ports 42, 44, and 46 could be fitted with flexible tubing for internal connection to other blood bags in a blood bag system. Bag 36 has an opening 54 at its bottom end for suspending the blood bag upside down. Flexible donor tubing 40 with conventional clamp 56 is integrally attached at one end to bag 36 and has needle assembly 10 at its opposite end. The blood bag system as shown in FIG. 3 when assembled may be sterilized as is customary in the art.

When blood is to be taken from a donor, retaining means 16 is grasped in one hand at its handle or hub portion. Flanges 32 and 34 on the needle protector are grasped with the other hand and twisted so as to rupture groove 24. The front portion of the needle assembly (needle protector with member 22 and a portion of the retaining means) is detached by pulling from the assembly thereby exposing the needle surface. Member 22 slides over the needle surface and removes a substantial portion of any liquid on the needle surface. The needle is then used in the venipuncture operation to withdraw blood from a donor. When an appropriate amount of blood is drawn, clamp 56 can be closed to stop the flow of blood from the donor. Needle 12 may then be inserted back into member 22 within the removed needle protector thus aiding in cleanliness and safety.

Figure 7:
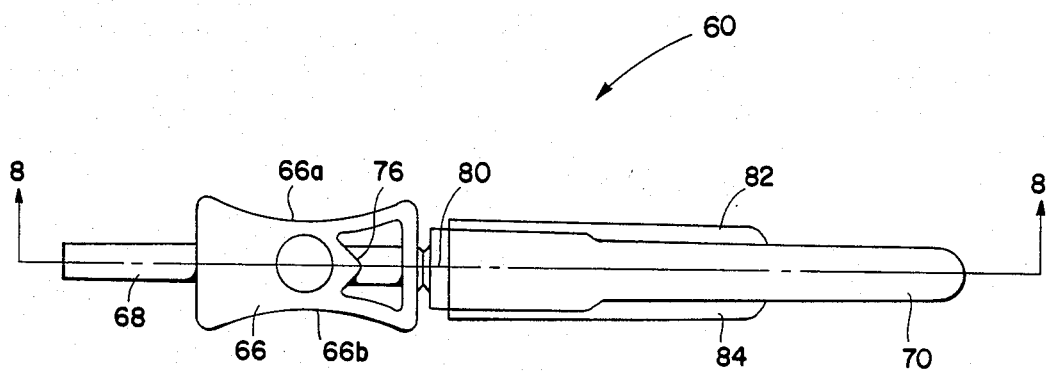
FIG. 7 is a top plan view of an alternate embodiment of the needle assembly.
Figure 8:
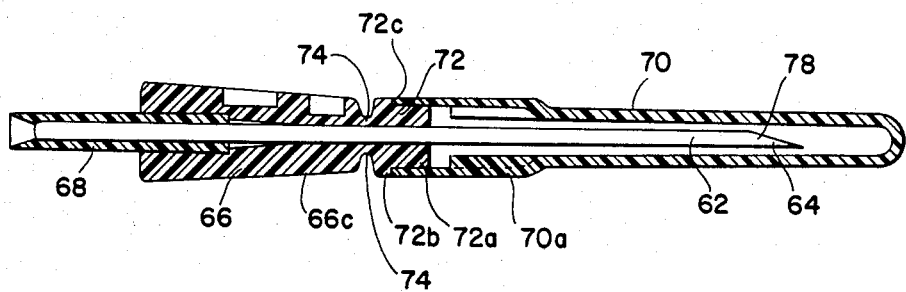
FIG. 8 is a cross sectional view taken along line 8—8 of FIG. 7.

The details of another embodiment of the needle assembly of the invention are best seen in FIGS. 7 and 8. As shown in these figures the needle assembly 60 includes a needle 62 sharpened at its forward end 64. At its rearward end the needle is permanently retained in a bore in a needle-retaining means 66, which has indentations 66a and 66b and thus may also serve as a handle or hub section to be grasped in the use of assembly 60. Preferably, means 66 has a slanted bottom surface 66c so that means 66 may fit closely to a donor's arm when the needle assembly is in use. The needle is retained in 66 by means of an adhesive or the like or other suitable modes of retention known in the art. Retaining means 66 is formed from a non-rigid material such as a medically acceptable elastomer or non-rigid thermoplastic, for example, polystyrene, polycarbonate, polyvinylchloride, and the like. Retaining means 66 has a narrow, tube-receiving section 68 at its rear designed to fit inside 66 in which it is retained by means of adhesive or the like or other suitable modes of retention. Section 68 is designed also to fit inside flexible tubing such as that found on a blood bag. Thus, the needle's passage is directly connected through section 68 to the passage of such flexible tubing. The forward part of means 66 is designed to receive needle protector 70, which surrounds needle 62 and protects the needle's sterility. Protector 70 is bonded to retaining means 66 by means of an adhesive or other suitable bonding material. Generally, needle protector 70 is formed of a rigid plastic or non-rigid plastic such as that used for needle-retaining means 66. Once assembled, the combination of needle protector 70 and retaining means 66 acts as a one-piece unit.

Surrounding needle 62 at its rearward end at a point near the handle or hub section is flexible resilient portion 72 of retaining means 66 made, of course, of the same non-rigid material. Portion 72 of 66 has a needle-accommodating opening having a diameter approximately that of the outside diameter of needle 62, thus providing a positioning of the needle-contacting portion of portion 72 about needle 62 and exerting a certain inward pressure on needle 62 such that liquid on the surface of the needle will be removed as portion 72 is disengaged from needle 62. Thus, as described above in FIGS. 1-5 the diameter of the opening should be such as to provide a gentle, liquid-removing wiping action on the needle surface without causing damage to the needle surface including any lubricant on the needle surface such as a silicone coating. Preferably, the opening of 72 should be slightly smaller, about 4-10%, than the outside diameter of the needle. In another preferred arrangement the diameter of the opening is such that the lubricating coating on the needle surface is distributed evenly by the action of member 72, thus providing a significant reduction, usually about 25% or more, in the shaft drag of the needle upon its insertion into the arm of a donor.

Needle-retaining means 66 has a narrowed portion at a point immediately rearward of needle protector 70, with peripheral, frangile, circumferential groove 74 which provides for a thickness preferably of about 0.012±0.001 mm at its narrowest point. In general, groove 74 is designed to facilitate the removal of needle protector 70 and portion 72 of means 66 from needle assembly 60 by twisting to rupture groove 74. In this way portion 72 acts in a manner previously described for member 22.

As can be seen from FIGS. 7 and 8 the rearward portion 70a of protector 70 is flanged outwardly such that the inside diameter of the rear portion of 70 is larger than the inside diameter of the front portion of 70. Portion 72 is positioned partly within the rearward portion of protector 70. Thus, portion 72 of 66 has a front part 72a having an outside diameter about equal to the inside diameter of protector 70 into which 72a is secured as mentioned above. The bottom part 72b of 72 has an outside diameter about equal to the outside diameter of 70a thus producing ledge part 72c similar to that found in FIGS. 2 and 3.

Needle assembly 70 additionally includes an arrowhead 76, in retaining means 66 to show the orientation of bevel 78 of the sharpened end of the needle when it is hidden from view, e.g., by being placed in the arm of a donor. The point of 76 may also be aligned during assembly with line marker 80 forward of groove 74. In this respect 76 in conjuction with line 80 acts to provide a tamper-evident feature to assembly 60. Thus, it may be readily evident to the user, simply by tactily sensing the integrity of groove 74 and/or looking at the position of 76 and 80, whether the needle assembly has been tampered with and sterility breached.

In the above there has been described a particular tamper-evident feature, which renders the needle assembly tamper-proof. As with the previously described embodiments of this invention, it is of course possible to employ another tamper-evidencing feature in the needle assembly.

Protector 70 further comprises integral flanges 82 and 84 which provide suitable gripping means for rotating the protector to disengage the front portion of the needle assembly from the rear portion along groove 74.

Figure 6:
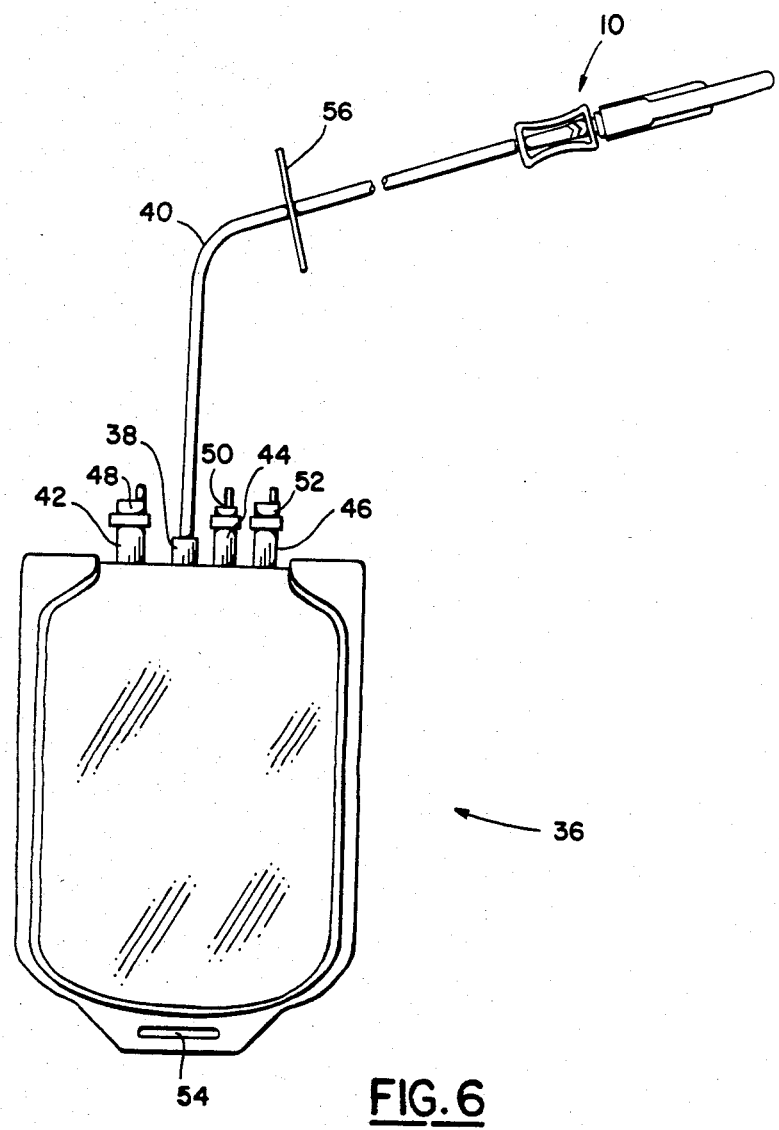
FIG. 6 is a front elevational view of a blood bag including the needle assembly of the invention.

It should be obvious that needle assembly 60 may be substituted for needle assembly 10 in FIG. 6.

We claim:

1. A needle assembly comprising a needle, a needle-retaining portion, a removable needle protector portion, and a resilient member for removing liquid from the surface of said needle, at least a portion of said liquid-removing member being contained within and removable with said needle protector portion and being positioned around a portion of, and disposed rearward of the point of, said needle, said liquid-removing member further having a needle-accommodating opening with an inner diameter approximately that of the outside diameter of the needle and outer cross sectional dimensions such that at least one of the dimensions is less than the internal cross sectional dimension of the protector, thereby providing a passageway for facilitating steam sterilization rearward of the liquid-removing member.

2. The assembly of claim 1 wherein the resilient member is a rubber septum.

3. The assembly of claim 1 wherein the resilient member is a rubber ring.

4. The assembly of claim 1 wherein the needle-retaining portion and the needle protector portion are separable from each other along a frangible, circumferential groove.

5. The assembly of claim 1 wherein the needle protector further includes flanges to facilitate gripping of the needle protector portion.

6. The assembly of claim 1 wherein the needle-retaining portion further includes opposed, laterally-indented portions to facilitate gripping of the needle-retaining portion.

7. The assembly of claim 1 which further includes a tamper-evident indicator.

8. The assembly of claim 1 wherein the needle-retaining portion further includes a flexible-tube-receiving section.

9. The assembly of claim 1 wherein said resilient member is an integral part of said needle-retaining portion but separable therefrom and removable with said needle-protecting portion.

10. A blood bag assembly comprising a donor bag and the needle assembly of claim 1 or claim 9.

11. The blood bag assembly of claim 10 which further comprises at least one satellite bag.

12. In a needle and needle protector combination including a needle-retaining portion permanently secured to the needle and separable from a needle protector portion along a frangible circumferential groove, the improvement which comprises a resilient member for removing liquid from the surface of said needle, at least a portion of said liquid-removing member being contained within said needle protector portion and removable from the combination with said needle protector portion and disposed rearward of the point of said needle, said liquid-removing member further having a needle-accommodating opening with an inner diameter such that a gentle, liquid-removing wiping action is exerted on the needle surface without damage to the surface of the needle and outer cross sectional dimensions such that at least one of the dimensions is less than the internal cross sectional dimension of the protector, thereby providing a passageway facilitating steam sterilization rearward of the liquid-removing member.

13. The combination of claim 12 wherein said resilient member is an integral part of said needle-retaining portion but separable therefrom and removable with said needle-protecting portion.

14. A blood bag assembly comprising a donor bag and the needle and needle protector combination of claim 12 or claim 13.

15. The blood bag assembly of claim 14 which further comprises at least one satellite bag.

16. The needle and needle protector combination of claim 12 wherein the needle-accommodating opening has a diameter which further provides for evenly distributing lubricant on the surface of the needle.

* * * * *